US005453521A

United States Patent [19]

Gaullier et al.

[11] Patent Number: 5,453,521

[45] Date of Patent: Sep. 26, 1995

[54] PROCESS FOR OBTAINING 10-DEACETYLBACCATIN III

[75] Inventors: Jean-Claude Gaullier, Champs sur Marne; Bernadette Mandard, Alfortville; Rodolphe Margraff, Viry Chatillon, all of France

[73] Assignee: Rhone-Poulenc Rorer S.A., Antony Cedex, France

[21] Appl. No.: 122,624

[22] Filed: Sep. 17, 1993

Related U.S. Application Data

[63] Continuation-in-part of Ser. No. 10,083, Jan. 27, 1993.

[30] Foreign Application Priority Data

Oct. 5, 1992 [FR] France .................................. 92 11746

[51] Int. Cl.$^6$ .................................................. C07D 301/32

[52] U.S. Cl. ............................................ 549/541; 568/320

[58] Field of Search ............................ 549/541; 568/320

[56] References Cited

U.S. PATENT DOCUMENTS 4,206,221 6/1980 Miller et al. ............................ 424/278

*Primary Examiner*—José G. Dees
*Assistant Examiner*—Joseph M. Conrad, III
*Attorney, Agent, or Firm*—Morgan & Finnegan

[57] ABSTRACT

Process for producing 10-deacetylbaccatin III from the various parts of the yew (Taxus sp.) by extraction and selective crystallization from a methanolic extract of the plant mass.

90 Claims, No Drawings

PROCESS FOR OBTAINING 10-DEACETYLBACCATIN III

The application is a continuation-in-part of Ser. No. 08/010,083, filed Jan. 27, 1993. This application is hereby incorporated by reference.

FIELD OF THE INVENTION

The present invention relates to a process for selectively obtaining intermediates which are useful for the preparation, by semi-synthetic processes, of taxol, Taxotere or their analogues from various parts of plants containing these intermediates.

More particularly, the invention relates to obtaining 10-deacetylbaccatin III from the bark, trunk, roots or leaves of various species of yew.

BACKGROUND OF THE INVENTION

Taxol and Taxotere as well as their analogues of general formulae:

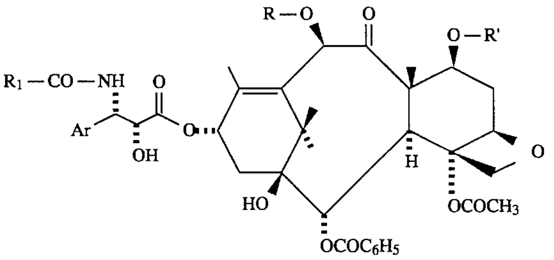

(I)

which show notable anticancer and antileukaemia properties, are notable chemotherapeutic agents for the treatment of a certain number of cancers such as, for example, cancers of the breast, prostate, colon, stomach, kidney or testicles and more especially cancer of the ovaries.

In particular, in the general formula (I), Ar can represent an optionally substituted phenyl radical, R can represent a hydrogen atom or an acetyl radical or an N-substituted carbamoyl radical, R' represents a hydrogen atom or an N-substituted carbamoyl radical and $R_1$ can represent a phenyl radical or a radical $R_2$—O— in which $R_2$ represents an alkyl, alkenyl, alkynyl, cycloalkyl, cycloalkenyl, bicycloalkyl, phenyl or heterocyclyl radical.

Taxol corresponds to the product of general formula (I) in which Ar and $R_1$ represent a phenyl radical and R represents an acetyl radical and R' represents a hydrogen atom and Taxotere corresponds to the product of general formula (I) in which Ar represents a phenyl radical, R and R' represent a hydrogen atom and $R_1$ represents a t-butoxy radical.

Taxol, which exists in the natural state in various species of yew in which it is found in small amounts, is difficult to isolate without completely destroying the plant. For example, taxol can be isolated according to the method of C. H. O. Huang et al., J. Natl. Prod., 49,665 (1986) which consists in treating the ground bark of Taxus brevifolia with methanol, in concentrating the extract, extracting the concentrate with dichloromethane, in again concentrating, in dispersing the residue in a hexane/acetone (1/1 by volume) mixture, and in purifying the soluble part by chromatography on a Florisil column to obtain crude taxol which is purified by successive recrystallizations from methanol/water and hexane/acetone mixtures, then by chromatography and again crystallization. The amounts of taxol thus extracted can represent from 0.005 to 0.017% of the part of the plant used.

Taxotere, which does not exist in the natural state, can be prepared by semi-synthesis from 10-deacetylbaccatin III of formula:

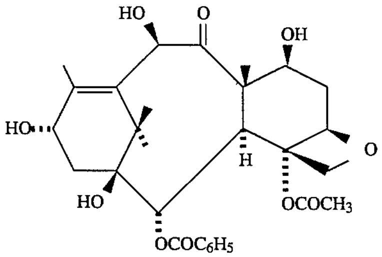

(II)

according to the processes which are described, for example, in American U.S. Pat. Nos. 4,814,470 or 4,924,012 or in International Application PCT WO 92/09589.

Taxol can also be prepared by the processes which involve the use of 10-deacetylbaccatin III, either by passing through the intermediacy of Taxotere under the conditions described in American U.S. Pat. No. 4,857,653 or by esterification of baccatin III under the conditions described in European Patents EP 400,971 or EP 428,376 or by esterification of 10-deacetylbaccatin III and acetylation under the conditions described in American U.S. Pat. No. 4,924,011.

The various varieties of yew (Taxus baccata, Taxus brevifolia, Taxus canadensis, Taxus cupidata, Taxus floridana, Taxus media and Taxus wallichiana) contain taxane derivatives, the main ones of which are essentially taxol and 10-deacetylbaccatin III, the other derivatives being more particularly cephalomannin, 10-deacetyl-cephalomannin or baccatin III, optionally linked to sugars.

Whilst taxol is mainly found in the trunk and bark, 10-deacetylbaccatin III is essentially present in the leaves. Moreover, the 10-deacetylbaccatin III content in the leaves is generally much greater than that of taxol, whether the latter is present in the bark, trunk or in the leaves.

It results therefore that it is particularly important to be able to have available 10-deacetylbaccatin III which is essential to the preparation of much more significant amounts of taxol than by direct extraction from yews as well as to the preparation of Taxotere.

The extraction of 10-deacetylbaccatin III from yew leaves does not lead to complete destruction of the plant, whose leaves can be used again after each growth cycle.

Generally, the known methods for extracting taxane derivatives contained in various parts of the yew (bark, trunk, roots, leaves and the like) require the use of lengthy and expensive chromatographic techniques which do not make possible complete and quantitative separation of the taxane derivatives initially present in the plant.

According to the process described in American U.S. Pat. No. 4,814,470, which uses maceration of the needles in ethanol, extraction with an organic solvent, such as methylene chloride, and successively chromatographing, it is possible to isolate approximately 40% of the 10-deacetylbaccatin III contained in the leaves.

The various taxane-derived constituents present in the various parts of the yew can also be separated by methods using "reverse" liquid phase chromatography which are described, in particular, in International Application PCT WO 92/07842. These processes consist essentially in treating the crude yew extracts by "reverse" liquid phase chromatography through an adsorbent on which the taxane derivatives are fixed, eluting the taxane derivatives and in isolating them. According to this process, it is possible to isolate approximately 25% of the 10-deacetylbaccatin III contained in the leaves.

DESCRIPTION OF THE INVENTION

It has now been found, and it is this which forms the subject of the present invention, that 10-deacetylbaccatin III can be selectively extracted from different parts of the yew, and more particularly from the leaves, by a simple process which does not use chromatographic techniques. For example, it is possible to extract approximately 75% of the 10-deacetylbaccatin III present in the leaves.

More particularly, the process according to the invention consists: either 1) in treating the ground parts of the yew (Taxus sp.) with an aliphatic alcohol so as to obtain an alcoholic extract containing 10-deacetylbaccatin III, 2) in diluting the optionally concentrated alcoholic extract with water, 3) in separating, by filtration, settling or centrifuging, the insoluble products present in the water/alcohol solution obtained, 4) in removing virtually all the alcohol from the water/alcohol solution, 5) in extracting 10-deacetylbaccatin III from the aqueous phase thus obtained with a suitable organic solvent, 6) in removing the solvent from the organic extract thus obtained containing 10-deacetylbaccatin III, 7) in selectively crystallizing 10-deacetylbaccatin III, in an organic solvent, in the residue thus obtained, 8) in isolating purified 10-deacetylbaccatin III, or else 1) in treating the ground parts of the yew (Taxus sp.) with an aliphatic alcohol so as to obtain an alcoholic extract containing 10-deacetylbaccatin III, 2) in extracting the alcoholic extract with an organic solvent, 3) in separating the water/alcohol phase obtained by settling, 4) in diluting the water/alcohol phase with water, 5) in separating, by filtration, settling or centrifuging, the insoluble products present in the water/alcohol solution obtained, 6) in extracting 10-deacetylbaccatin III from the filtered water/alcohol phase with an organic solvent, 7) in entirely or partially removing the solvent from the organic extract containing 10-deacetylbaccatin III, 8) in selectively crystallizing 10-deacetylbaccatin III, in an organic solvent, from the solution or the residue obtained, 9) in isolating purified 10-deacetylbaccatin III.

The process according to the invention can be used on any suitable part of the yew such as the bark, trunk, roots or leaves. The yew used for implementation of the process according to the invention preferably belongs to the variety *Taxus baccata, Taxus brevifolia, Taxus canadensis, Taxus cupidata, Taxus floridana, Taxus media* or *Taxus wallichiana*. It is particularly advantageous to use yew leaves (*Taxus baccata, Taxus brevifolia*) which generally are richer in 10-deacetylbaccatin III. For a better use of the process, it is preferable to use the various parts of the yew in the ground and optionally dried form. The fragments used can have sizes varying from 0.5 to several millimeters. For reasons of convenience, it can be advantageous to use fragments whose mean sizes are less than 1 mm. The ground and optionally dried parts of the yew can be obtained by grinding, and optionally drying, operations which, optionally, precede or follow freezing and defrosting operations of the fresh parts of the plant or are inserted into freezing and defrosting operations of the fresh parts of the plant.

The alcoholic extract is obtained by stirring an optionally heated mixture of the ground, and optionally dried, parts of the yew with an alcohol generally chosen from methanol, ethanol, propanol, isop ropanol, and t-butanol. It is particularly advantageous to use methanol.

The alcoholic extract containing 10-deacetylbaccatin III can be treated according to one of the following methods:

1) the alcoholic extract containing 10-deacetylbaccatin III is diluted by the addition of water to give a water/alcohol solution.

It is advantageous, for the implementation of the process, for it to take place under specific conditions of dilution and of alcohol content in the aqueous phase, so as to avoid 10-deacetylbaccatin III losses and to remove the greatest possible amount of insoluble products. Under these conditions, it may be necessary to concentrate the alcoholic extract containing 10-deacetylbaccatin III prior to diluting with water.

More particularly, dilution by addition of water to the alcoholic extract, optionally concentrated by distillation, preferably under reduced pressure, must be carried out in such a way that the ratio of the weight of the diluent mixture to the weight of the solids contained in the alcoholic extract is between 4 and 8, the water/alcohol diluent mixture containing 10 to 30% by weight of alcohol.

The insoluble products in the water/alcohol solution thus obtained are removed according to the usual techniques and preferably by filtration, settling or centrifuging. When removal is carried out by filtration, it can be advantageous to carry out the filtration in the presence of a filtration agent, such as diatomaceous earth (Celite), and a flocculating agent.

Preferably, removal of the alcohol from the Water/alcohol solution thus obtained is carried out by distillation, preferably under reduced pressure, optionally in the presence of an antifoaming agent, so as to prevent or limit thermal degradation of the constituents of the medium.

Generally, 10-deacetylbaccatin III contained in the aqueous solution thus obtained, in which the alcohol content is generally less than 1%, is extracted, once or a number of times, with an organic solvent chosen from ethers, Such as methyl t-butyl ether, ethyl t-butyl ether, methyl n-butyl ether, methyl n-amyl ether, ethyl t-amyl ether, t-butyl isopropyl ether, ethyl isobutyl ether, t-butyl n-propyl ether or ethyl n-hexyl ether, and aliphatic esters, such as ethyl acetate, propyl acetate, isopropyl acetate, n-butyl acetate, t-butyl acetate, methyl t-butylacetate, t-butyl propionate or t-amyl acetate. Very particularly advantageous are methyl t-butyl ether, ethyl t-butyl ether, ethyl acetate or n-butyl acetate. More particularly still, it is advantageous to use ethyl acetate or n-butyl acetate, 2) the alcoholic extract, which contains water arising from the yew leaves used, is extracted with a suitable organic solvent chosen from aromatic hydrocarbons such as toluene or xylene.

The water/alcohol extract is diluted by the addition of water, so that the extract contains from 20 to 40% alcohol, and it is then filtered or settled or centrifuged to separate the insoluble products present. The water/alcohol solution obtained, which contains 10-deacetylbaccatin III, is extracted once or a number of times with an organic solvent chosen from ethers, such as methyl t-butyl ether, ethyl t-butyl ether, methyl n-butyl ether, methyl n-amyl ether, ethyl t-amyl ether, t-butyl isopropyl ether, ethyl isobutyl ether, t-butyl n-propyl ether or ethyl n-hexyl ether, and aliphatic esters, such as ethyl acetate, propyl acetate, isopropyl acetate, n-butyl acetate, t-butyl acetate, methyl t-butylacetate, t-butyl propionate or t-amyl acetate. Very particularly advantageous are methyl t-butyl ether, ethyl t-butyl ether, ethyl acetate or n-butyl acetate. More especially still, it is advantageous to use ethyl acetate or n-butyl acetate.

The organic extracts, obtained according to either route, are optionally washed using an aqueous solution of a weak base (aqueous sodium carbonate solution, for example) and/or with water. After optional drying, the organic solvent of the extract is entirely or partially removed according to the usual methods and in particular by distillation, optionally under reduced pressure, to give a solution or generally solid residue from which 10-deacetylbaccatin III is isolated.

Selective crystallization of 10-deacetylbaccatin III is carried out from a solution in an organic solvent or in a mixture of organic solvents. There can advantageously be used, as solvents which make possible selective crystallization of 10-deacetylbaccatin III, nitriles such as acetonitrile or propionitrile, optionally as a mixture with an aliphatic alcohol such as methanol, ethanol, propanol, isopropanol or n-butanol or an aliphatic ester such as ethyl acetate, isopropyl acetate, n-butyl acetate or t-butyl acetate or a ketone such as acetone, methyl ethyl ketone, methyl propyl ketone, methyl n-butyl ketone and methyl isobutyl ketone. It is particularly advantageous to carry out the selective crystallization from acetonitrile, optionally in the presence of ethanol and/or acetone and/or ethyl acetate and/or n-butyl acetate.

10-Deacetylbaccatin III, which precipitates, can be isolated by filtration, settling or centrifuging.

10-Deacetylbaccatin III obtained according to the extraction process of the present invention can be used to prepare taxol or Taxotere or their derivatives under the conditions described more particularly in Patents EP 0,253,738, EP 0,253,739, EP 0,336,840, EP 0,336,841, WO 92 09589, EP 0,400,971 and EP 0,428,376.

EXAMPLES

The following examples illustrate the process according to the invention.

EXAMPLE 1

200 liters of methanol, 1.4 kg of glass wool and 250 kg of ground yew (Taxus baccata) leaves, the mean size of the particles of which is in the region of 0.8 mm, are placed in a percolator. 400 liters of pure methanol are added. Percolation is carried out by supplying the percolator with fresh solvent near the top, at a flow rate of 870 liters/hour, and by collecting the methanol extract at the bottom of the percolator. Percolation lasts 5 hours at 20° C. The methanol solution collected is evaporated under reduced pressure (70–80 kPa) at 40° C. in an evaporator to produce a concentrate whose solids content is between 40 and 80% by weight.

A methanol extract (prepared under the conditions described above) is used containing 353 g of solids, 420 g of methanol and 40 g of water, the amount of 10-deacetylbaccatin III present being 1130 mg.

The methanol extract is introduced into a 2 liter reactor and then 1590cm$^3$ of water are introduced with stirring. The mixture is stirred for 1 hour and then 35 g of Celite, whilst stirring for 1 hour, and 25 cm$^3$ of "Zetag 87" flocculating agent are added successively. The final suspension obtained is filtered through sintered glass No. 4 with a diameter of 130 mm. The insoluble products and the Celite are washed with 100 g of a water/methanol (8/2 by weight) mixture.

The filtrate is placed in a 2 liter reactor and then 2 cm$^3$ of silicone 426R are added. The mixture is distilled under reduced pressure (7.3–11 kPa) at a temperature of between 35° and 42° C., the external bath temperature being between 45° and 50° C. A distillate (909 g) and a concentrate (1432 g) containing 0.5% of methanol are obtained.

The concentrate is extracted once with 700 cm$^3$ of ethyl acetate and then twice with 350 cm$^3$ of ethyl acetate. The combined organic phases are washed twice with 700 cm$^3$ of a 0.1M sodium carbonate solution and then with i×350 cm$^3$ of water. The pH is equal to 8. The organic phase (1049 g) is concentrated to 1 times dryness under reduced pressure (1.33–21.3 kPa) at 40° C. 16.2 g of solids are thus obtained.

EXAMPLE 2

45.5 g of solids containing 9.3% of 10-deacetylbaccatin III obtained under the conditions described in Example I are introduced into a 500 cm$^3$ round-bottomed flask and then 18 cm$^3$ of ethyl acetate are added. The homogenous mixture is stirred and heated to 50° C. 136 cm$^3$ of acetonitrile are then added over 15 minutes at 50° C. The suspension is stirred for approximately 1 hour and it is then cooled to a temperature in the region of 20° C. over approximately 3 hours. The precipitate is separated by filtering through sintered glass No. 3 (diameter: 35 mm), then it is washed with 20 cm$^3$ of acetonitrile and then with 2 times 20 cm$^3$ of diisopropyl ether. The product is dried under reduced pressure (1.33 kPa) at 40° C. for 20 hours. There are thus obtained 5.2 g of a white product containing 75.8% of 10-deacetylbaccatin III.

The yield from the crystallization is 93.6%.

EXAMPLE 3

275.2 g of a solution in ethyl acetate of 39.6 g of solids containing 3.48 g of 10-deacetylbaccatin III are introduced into a 1 liter round-bottomed flask. This solution is concentrated under reduced pressure (6.0 kPa). 164 g of ethyl acetate are collected. 36 cm$^3$ of ethanol are added to the concentrate and then cooling is carried out to 10° C. 60 cm$^3$ of acetonitrile are then slowly added (approximately ½ hour) with stirring (30 revolutions/minute). The suspension is stirred for 1 hour at 10° C. and then 84 cm$^3$ of acetonitrile are rapidly added. Stirring is carried out for 15 hours at 10° C. The precipitate is separated by filtering through sintered glass No. 3 (diameter: 35 mm), then it is washed with 2 times 20 cm$^3$ of acetonitrile and then with 2 times 20 cm$^3$ of diisopropyl ether. The product is dried for 12 hours under reduced pressure (0.27 kPa) at 40° C. There are thus obtained 2.85 g of a crystalline white powder containing 93.8% of 10-deacetylbaccatin III.

The crystallization mother liquors and the washes (247 g) are concentrated under reduced pressure (2.7 kPa) at 40° C. There are thus obtained 36 g of dry substance which is taken up in 18 cm$^3$ of ethanol. 72 cm$^3$ of acetonitrile are then slowly added. The mixture is stirred for 15 hours at a temperature in the region of 20° C. The precipitate is separated by filtration and is washed with 2 times 5 cm$^3$ of acetonitrile and with 2 times 5 $cm^3$ of diisopropyl ether. After drying, there is obtained 0.66 g of a fine powder containing 62.7% of 10-deacetylbaccatin III.

EXAMPLE 4

A methanolic extract, prepared under the conditions described in Example 1, is used consisting of 1840 g of solids, 1117 g of methanol and 329 g of water and containing 7.17 g of 10-deacetylbaccatin III.

The methanolic extract is introduced into a 10 liter reactor and then extraction is carried out 3 times with 1.5 liter of toluene with vigorous stirring. The water/methanol phase is separated (3020 g) by settling, diluted by the addition of water (3800 g) and then filtered. 42 g of residue are thus separated.

The filtered water/methanol solution is extracted 3 times with 1540 $cm^3$ of n-butyl acetate. The combined organic phases are concentrated under reduced pressure (1.33 kPa) at 40° C. so as to obtain a solution containing 30% of solids and then filtered. The residue obtained (4 g) is washed with 50 $cm^3$ of n-butyl acetate. The organic filtrates are combined and concentrated again under reduced pressure (1.33 kPa) at 40° C. so as to obtain a solution containing 65% solids (i.e. 95 g).

The concentrate thus obtained is introduced into a 500 $cm^3$ round-bottomed flask. 45 $cm^3$ of ethanol are added. The homogeneous mixture is stirred and heated to 40° C. 270 $cm^3$ of acetonitrile are then added over 1 hour at 40° C. The suspension is cooled to −10° C., while continually stirring, over 2 hours and then maintained at −10° C. overnight. The precipitate is separated by filtering through sintered glass, washed twice with 35 $cm^3$ of acetonitrile, then with 2 times 35 $cm^3$ of diisopropyl ether and then dried overnight under reduced pressure (1.33 kPa) at 40° C.

There are thus obtained 5.92 g of a white product containing 84.2% of 10-deacetylbaccatin III.

The yield, with respect to 10-deacetylbaccatin III contained in the initial methanolic extract, is 69.5%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for obtaining 10-deacetylbaccatin III from the various parts of the yew (Taxus sp.), comprising:

1) treating the ground parts of the yew with an aliphatic alcohol so as to obtain an alcoholic extract containing 10-deacetylbaccatin III, 2) diluting the optionally concentrated alcoholic extract with water, 3) separating the insoluble products present in the water/alcohol solution obtained by filtration, settling or centrifuging, 4) removing virtually all the alcohol from the water/alcohol solution obtained, 5) extracting 10-deacetylbaccatin III contained in the aqueous phase thus obtained with a suitable organic solvent, 6) removing the solvent from the organic extract thus obtained, 7) selectively crystallizing 10-deacetylbaccatin III from the residue thus obtained and then, 8) isolating purified 10-deacetylbaccatin III.

2. Process for obtaining 10-deacetylbaccatin III from various parts of yew (Taxus sp.), comprising:

1) treating the ground parts of the yew with an aliphatic alcohol so as to obtain an alcoholic extract containing 10-deacetylbaccatin III, 2) extracting the alcoholic extract with an organic solvent, 3) separating the water/alcohol phase obtained by settling, 4) diluting the water/alcohol phase with water, 5) separating the insoluble products present in the water/alcohol solution obtained by filtration, settling or centrifuging, 6) extracting 10-deacetylbaccatin III from the filtered water/organic phase with an organic solvent, 7) removing the solvent entirely or partially from the organic extract containing 10-deacetylbaccatin III, 8) selectively crystallizing 10-deacetylbaccatin III in an organic solvent, from the solution or residue obtained, and 9) isolating 10-deacetylbaccatin III.

3. Process according to either of claims 1 or 2, wherein the alcoholic extract is obtained by stirring the ground, and optionally dried, parts of the yew in an aliphatic alcohol selected from methanol, ethanol, propanol, isopropanol and t-butanol.

4. Process according to claim 3, wherein the optionally concentrated methanolic extract is diluted with water so that the ratio of the weight of the diluent mixture to the weight of the solids contained in the alcoholic extract is between 4 and 8 and the water/alcohol diluent mixture contains 10 to 30% of alcohol to obtain a water/alcohol solution.

5. Process according to claim 3, wherein the insoluble products are separated from the water/alcohol solution by filtration, settling or centrifuging.

6. Process according to claim 3, wherein 10-deacetylbaccatin III is extracted from the aqueous phase, obtained after removal of the alcohol, with an organic solvent.

7. Process according to claim 3, wherein the alcohol is removed from the water/alcohol solution by distillation, optionally under reduced pressure.

8. Process according to claim 3, wherein the alcoholic phase is extracted with an organic solvent selected from aromatic hydrocarbons.

9. Process according to claim 8, wherein the aromatic hydrocarbon is selected from toluene and xylene.

10. Process according to claim 3, wherein the water/alcohol phase, separated by settling, is diluted by addition of water so that the alcohol content in the solution is between 20 and 40% by weight.

11. Process according to claim 3, wherein the insoluble products are separated from the diluted water/alcohol solution by filtration, settling or centrifuging.

12. Process according to claim 3, wherein 10-deacetylbaccatin III is extracted from the water/alcohol phase with an organic solvent.

13. Process according to claim 3, wherein the organic extract containing 10-deacetylbaccatin III is entirely or partially concentrated by distillation, optionally under reduced pressure.

14. Process according to claim 3, wherein 10-deacetylbaccatin III is selectively crystallized from an organic solvent selected from aliphatic nitriles, optionally mixed with an aliphatic alcohol or an aliphatic ester or an aliphatic ketone.

15. Process according to claim 14, wherein the aliphatic nitriles are selected from acetonitrile and propionitrile.

16. Process according to claim 14, wherein the aliphatic alcohol is selected from methanol, ethanol, propanol, isopropanol or n-butanol.

17. Process according to claim 14, wherein the aliphatic ester is selected from ethyl acetate, isopropyl acetate, n-butyl acetate and t-butyl acetate.

18. Process according to claim 14, wherein the ketone is selected from acetone, methyl ethyl ketone, methyl propyl ketone, methyl n-butyl ketone and methyl isobutyl ketone.

19. Process according to claim 14, wherein selective crystallization is carried out from acetonitrile, optionally in combination with ethanol and/or ethyl or n-butyl acetate and/or acetone.

20. Process according to claim 3, wherein purified 10-deacetylbaccatin III is isolated by filtration, settling or centrifuging.

21. Process according the claim 3, wherein the aliphatic alcohol is methanol.

22. Process according to claim 21, wherein the optionally concentrated methanolic extract is diluted with water so that the ratio of the weight of the diluent mixture to the weight of the solids contained in the alcoholic extract is between 4 and 8 and the water/alcohol diluent mixture contains 10 to 30% of alcohol to obtain a water/alcohol solution.

23. Process according to claim 21, wherein the insoluble products are separated from the water/alcohol solution by filtration, settling or centrifuging.

24. Process according to claim 21, wherein the alcohol is removed from the water/alcohol solution by distillation, optionally under reduced pressure.

25. Process according to claim 21, wherein 10-deacetylbaccatin III is extracted from the aqueous phase, obtained after removal of the alcohol, with an organic solvent.

26. Process according to claim 21, wherein the alcoholic phase is extracted with an organic solvent selected from aromatic hydrocarbons.

27. Process according to claim 26, wherein the aromatic hydrocarbon is selected from toluene and xylene.

28. Process according to claim 21, wherein the water/alcohol phase, separated by settling, is diluted by addition of water so that the alcohol content in the solution is between 20 and 40% by weight.

29. Process according to claim 21, wherein the insoluble products are separated from the diluted water/alcohol solution by filtration, settling or centrifuging.

30. Process according to claim 21, wherein 10-deacetylbaccatin III is extracted from the water/alcohol phase with an organic solvent.

31. Process according to claim 21, wherein the organic extract containing 10-deacetylbaccatin III is entirely or partially concentrated by distillation, optionally under reduced pressure.

32. Process according to claim 21, wherein 10-deacetylbaccatin III is selectively crystallized from an organic solvent selected from aliphatic nitriles, optionally mixed with an aliphatic alcohol or an aliphatic ester or an aliphatic ketone.

33. Process according to claim 32, wherein the aliphatic nitriles are selected from acetonitrile and propionitrile.

34. Process according to claim 32, wherein the aliphatic alcohol is selected from methanol, ethanol, propanol, isopropanol or n-butanol.

35. Process according to claim 32, wherein the aliphatic ester is selected from ethyl acetate, isopropyl acetate, n-butyl acetate and t-butyl acetate.

36. Process according to claim 32, wherein the ketone is selected from acetone, methyl ethyl ketone, methyl propyl ketone, methyl n-butyl ketone and methyl isobutyl ketone.

37. Process according to claim 32, wherein selective crystallization is carried out from acetonitrile, optionally in combination with ethanol and/or ethyl or n-butyl acetate and/or acetone.

38. Process according to either of claims 1 or 2, wherein the ground, and optionally dried, parts of the yew are obtained by grinding, and optionally drying, operations which optionally precede or follow freezing and defrosting operations of the fresh parts of the plant or are inserted into freezing and defrosting operations of the fresh parts of the plant.

39. Process according to claim 38, wherein the optionally concentrated methanolic extract is diluted with water so that the ratio of the weight of the diluent mixture to the weight of the solids contained in the alcoholic extract is between 4 and 8 and the water/alcohol diluent mixture contains 10 to 30% of alcohol to obtain a water/alcohol solution.

40. Process according to claim 38, wherein the insoluble products are separated from the water/alcohol solution by filtration, settling or centrifuging.

41. Process according to claim 38, wherein the alcohol is removed from the water/alcohol solution by distillation, optionally under reduced pressure.

42. Process according to claim 38, wherein 10-deacetylbaccatin III is extracted from the aqueous phase, obtained after removal of the alcohol, with an organic solvent.

43. Process according to claim 38, wherein the alcoholic phase is extracted with an organic solvent selected from aromatic hydrocarbons.

44. Process according to claim 43, wherein the aromatic hydrocarbon is selected from toluene and xylene.

45. Process according to claim 38, wherein the water/alcohol phase, separated by settling, is diluted by addition of water so that the alcohol content in the solution is between 20 and 40% by weight.

46. Process according to claim 38, wherein the insoluble products are separated from the diluted water/alcohol solution by filtration, settling or centrifuging.

47. Process according to claim 38, wherein 10-deacetylbaccatin III is extracted from the water/alcohol phase with an organic solvent.

48. Process according to claim 38, wherein the organic extract containing 10-deacetylbaccatin III is entirely or partially concentrated by distillation, optionally under reduced pressure.

49. Process according to claim 38, wherein 10-deacetylbaccatin III is selectively crystallized from an organic solvent selected from aliphatic nitriles, optionally mixed with an aliphatic alcohol or an aliphatic ester or an aliphatic ketone.

50. Process according to claim 49, wherein the aliphatic nitriles are selected from acetonitrile and propionitrile.

51. Process according to claim 49, wherein the aliphatic alcohol is selected from methanol, ethanol, propanol, isopropanol or n-butanol.

52. Process according to claim 49, wherein the aliphatic ester is selected from ethyl acetate, isopropyl acetate, n-butyl acetate and t-butyl acetate.

53. Process according to claim 49, wherein the ketone is selected from acetone, methyl ethyl ketone, methyl propyl ketone, methyl n-butyl ketone and methyl isobutyl ketone.

54. Process according to claim 49, wherein selective crystallization is carried out from acetonitrile, optionally in combination with ethanol and/or ethyl or n-butyl acetate and/or acetone.

55. Process according to claim 38, wherein purified 10-deacetylbaccatin III is isolated by filtration, settling or centrifuging.

56. Process according to claim 2, wherein the alcoholic phase is extracted with an organic solvent selected from aromatic hydrocarbons.

57. Process according to claim 56, wherein the aromatic hydrocarbon is selected from toluene and xylene.

58. Process according to claim 2, wherein the water/alcohol phase, separated by settling, is diluted by addition of water so that the alcohol content in the solution is between 20 and 40% by weight.

59. Process according to claim 2, wherein the insoluble products are separated from the diluted water/alcohol solution by filtration, settling or centrifuging.

60. Process according to claim 2, wherein 10-deacetylbaccatin III is extracted from the water/alcohol phase with an organic solvent.

61. Process according to claim 60, wherein the solvent is selected from ethers and aliphatic esters.

62. Process according to claim 61, wherein the ethers are selected from methyl t-butyl ether, ethyl t-butyl ether, methyl n-butyl ether, methyl n-amyl ether, ethyl t-amyl ether, t-butyl isopropyl ether, ethyl isobutyl ether, t-butyl n-propyl ether and ethyl n-hexyl ether.

63. Process according to claim 62, wherein the aliphatic esters are selected from ethyl acetate, propyl acetate, isopropyl acetate, n-butyl acetate, t-butyl acetate, methyl t-butylacetate, t-butyl propionate and t-amyl acetate.

64. Process according to claim 62, wherein the organic solvent is ethyl acetate or n-butyl acetate.

65. Process according to claim 2, wherein the organic extract containing 10-deacetylbaccatin III is entirely or partially concentrated by distillation, optionally under reduced pressure.

66. Process according to claim 2, wherein 10-deacetylbaccatin III is selectively crystallized from an organic solvent selected from aliphatic nitriles, optionally mixed with an aliphatic alcohol or an aliphatic ester or an aliphatic ketone.

67. Process according to claim 66, wherein the aliphatic nitriles are selected from acetonitrile and propionitrile.

68. Process according to claim 66, wherein the aliphatic alcohol is selected from methanol, ethanol, propanol, isopropanol or n-butanol.

69. Process according to claim 66, wherein the aliphatic ester is selected from ethyl acetate, isopropyl acetate, n-butyl acetate and t-butyl acetate.

70. Process according to claim 66, wherein the ketone is selected from acetone, methyl ethyl ketone, methyl propyl ketone, methyl n-butyl ketone and methyl isobutyl ketone.

71. Process according to claim 66, wherein selective crystallization is carried out from acetonitrile, optionally in combination with ethanol and/or ethyl or n-butyl acetate and/or acetone.

72. Process according to claim 2, wherein purified 10-deacetylbaccatin III is isolated by filtration, settling or centrifuging.

73. Process according to claim 1, wherein the optionally concentrated methanolic extract is diluted with water so that the ratio of the weight of the diluent mixture to the weight of the solids contained in the alcoholic extract is between 4 and 8 and the water/alcohol diluent mixture contains 10 to 30% of alcohol to obtain a water/alcohol solution.

74. Process according to claim 1, wherein the insoluble products are separated from the water/alcohol solution by filtration, settling or centrifuging.

75. Process according to claim 1, wherein the alcohol is removed from the water/alcohol solution by distillation, optionally under reduced pressure.

76. Process according to claim 1, wherein 10-deacetylbaccatin III is extracted from the aqueous phase, obtained after removal of the alcohol, with an organic solvent.

77. Process according to claim 76, wherein the organic solvent is selected from ethers and aliphatic esters.

78. Process according to claim 77, wherein the ethers are selected from methyl t-butyl ether, ethyl t-butyl ether, methyl n-butyl ether, methyl n-amyl ether, ethyl t-amyl ether, t-butyl isopropyl ether, ethyl isobutyl ether, t-butyl n-propyl ether and ethyl n-hexyl ether.

79. Process according to claim 76, wherein the aliphatic esters are selected from ethyl acetate, propyl acetate, isopropyl acetate, n-butyl acetate, t-butyl acetate, methyl t-butylacetate, t-butyl propionate and t-amyl acetate.

80. Process according to claim 76, wherein the organic solvent is ethyl acetate or n-butyl acetate.

81. Process according to claim 1, wherein 10-deacetylbaccatin III is selectively crystallized from an organic solvent selected from aliphatic nitriles, optionally mixed with an aliphatic alcohol or an aliphatic ester or an aliphatic ketone.

82. Process according to claim 81, wherein the aliphatic nitriles are selected from acetonitrile and propionitrile.

83. Process according to claim 81, wherein the aliphatic alcohol is selected from methanol, ethanol, propanol, isopropanol or n-butanol.

84. Process according to claim 81, wherein the aliphatic ester is selected from ethyl acetate, isopropyl acetate, n-butyl acetate and t-butyl acetate.

85. Process according to claim 81, wherein the ketone is selected from acetone, methyl ethyl ketone, methyl propyl ketone, methyl n-butyl ketone and methyl isobutyl ketone.

86. Process according to claim 81, wherein selective crystallization is carried out from acetonitrile, optionally in combination with ethanol and/or ethyl or n-butyl acetate and/or acetone.

87. Process according to claim 1, wherein purified 10-deacetylbaccatin III is isolated by filtration, settling or centrifuging.

88. Process according to claim 21, wherein purified 10-deacetylbaccatin III is isolated by filtration, settling or centrifuging.

89. Process according to one of claims 1, 23, 73, 74, 75, 76, 77, 78, 79, 38, 56, 57, 9, 58, 59, 60, 61, 62, 63, 64, 65, 81, 66, 67, 83, 68, 84, 69, 85, 70, 86, 71 or 87, wherein 10-deacetylbaccatin III is extracted from leaves of the yew.

90. Process according to claim 89, wherein the yew belongs to the variety *Taxus baccata, Taxus brevifloria, Taxus canadensis, Taxus cupidata, Taxus floridana, Taxus media* or *Taxus wallichiana*.

* * * * *

UNITED STATES PATENT AND TRADEMARK OFFICE

CERTIFICATE OF CORRECTION

PATENT NO. : 5,453,521

DATED : September 26, 1995

INVENTOR(S) : GAULLIER, MANDARD and MARGRAFF

It is certified that error appears in the above-identified patent and that said Letters Patent is hereby corrected as shown below:

Claim 89, col. 12, lines 54, "23" should read --2--.

Signed and Sealed this

Ninth Day of January, 1996

Attest:

BRUCE LEHMAN

Attesting Officer

Commissioner of Patents and Trademarks